US 6,709,457 B1

(12) United States Patent
Otte et al.

(10) Patent No.: US 6,709,457 B1
(45) Date of Patent: Mar. 23, 2004

(54) ATTACHMENT OF SUTURE CUFF TO PROSTHETIC HEART VALVE

(75) Inventors: John F. Otte, Mendota Heights, MN (US); Kimberly A. Anderson, Eagan, MN (US)

(73) Assignee: St. Jude Medical, Inc., St. Paul, MN (US)

(*) Notice: Subject to any disclaimer, the term of this patent is extended or adjusted under 35 U.S.C. 154(b) by 0 days.

(21) Appl. No.: 09/449,308

(22) Filed: Nov. 24, 1999

(51) Int. Cl.$^7$ .................................................. A61F 2/24
(52) U.S. Cl. ........................................................ 623/2.4
(58) Field of Search ................................. 623/2.4, 2.38, 623/2.36, 2.37, 2.28

(56) References Cited

U.S. PATENT DOCUMENTS

| 3,409,013 | A |   | 11/1968 | Berry ............................ 128/303 |
| 3,587,115 | A |   | 6/1971 | Shiley ................................ 3/1 |
| 3,781,969 | A | * | 1/1974 | Anderson ...................... 29/445 |
| 3,860,005 | A |   | 1/1975 | Anderson et al. ............ 128/303 |
| 4,078,268 | A |   | 3/1978 | Possis ............................. 3/1.5 |
| 4,643,732 | A | * | 2/1987 | Pietsch et al. .................. 623/2 |
| 4,680,031 | A |   | 7/1987 | Alonso ............................ 623/2 |
| 4,743,253 | A |   | 5/1988 | Magladry ....................... 623/2 |
| 4,801,015 | A |   | 1/1989 | Lubock et al. .............. 206/438 |
| 5,071,431 | A |   | 12/1991 | Sauter et al. ................... 623/2 |
| 5,163,955 | A |   | 11/1992 | Love et al. ..................... 623/2 |
| 5,236,450 | A |   | 8/1993 | Scott .............................. 623/2 |
| 5,443,502 | A |   | 8/1995 | Caudillo et al. ................ 623/2 |
| 5,480,425 | A |   | 1/1996 | Ogilive .......................... 623/2 |
| 5,612,885 | A |   | 3/1997 | Love ....................... 364/468.04 |
| 5,716,398 | A |   | 2/1998 | Sparks et al. .................. 623/2 |
| 5,716,401 | A |   | 2/1998 | Eberhardt et al. ............. 623/2 |
| 5,716,402 | A |   | 2/1998 | Reif ............................... 623/2 |
| 5,755,782 | A | * | 5/1998 | Love et al. ..................... 623/2 |
| 5,776,187 | A |   | 7/1998 | Krueger et al. ................ 623/2 |
| 5,788,689 | A |   | 8/1998 | Allan et al. .................... 606/1 |
| 5,824,066 | A |   | 10/1998 | Gross ............................. 623/2 |
| 5,824,068 | A |   | 10/1998 | Bugge ........................... 623/2 |
| 5,843,158 | A |   | 12/1998 | Lenker et al. ................. 623/1 |
| 5,843,178 | A |   | 12/1998 | Vanney et al. ................. 623/2 |
| 5,843,179 | A | * | 12/1998 | Vanney et al. ................. 623/2 |
| 6,059,827 | A | * | 5/2000 | Fenton, Jr. ..................... 623/2 |
| 6,241,765 | B1 | * | 6/2001 | Griffin et al. .............. 623/2.38 |
| 6,334,873 | B1 | * | 1/2002 | Lane et al. ................ 623/2.14 |

FOREIGN PATENT DOCUMENTS

GB          2 181 057 A        4/1987

* cited by examiner

Primary Examiner—Corrine McDermott
Assistant Examiner—Alvin Stewart
(74) Attorney, Agent, or Firm—Altera Law Group, LLC; Hallie A. Finucane

(57) ABSTRACT

A prosthetic heart valve having an orifice is configured to allow blood flow through an orifice. A suture cuff extends around an outer circumference of an outer ring. The suture cuff is adapted for attachment to a native tissue annulus of a patient. A weld between the suture cuff and the ring is configured to attach the suture cuff to the ring.

43 Claims, 7 Drawing Sheets

ATTACHMENT OF SUTURE CUFF TO PROSTHETIC HEART VALVE

FIELD OF THE INVENTION

The present invention relates to prosthetic heart valves. More specifically, the present invention relates to attachment of a suture cuff to the prosthetic heart valve.

BACKGROUND OF THE INVENTION

Prosthetic heart valves are used to replace defective natural heart valves in patients. The defective natural heart valve is excised by a surgeon and the replacement prosthetic heart valve is attached to the native tissue annulus in the patient's heart. The prosthetic heart valve includes some type of occluding device, such as a pair of leaflets, which allows blood flow in one direction and blocks blood flow in the other direction.

Most prosthetic heart valves include a sewing or suture cuff, which extends around an outer circumference of the valve. The suture cuff is used to attach the prosthetic heart valve to the native tissue annulus. The suture cuff typically comprises a fabric material, which is configured to be sutured to the native tissue annulus using known techniques.

The suture cuff is attached to the heart valve using techniques such as those illustrated in U.S. Pat. No. 3,781,969 to Anderson issued Jan. 1, 1974. In Anderson, cords 57 are wrapped around the interior of the suture cuff, which secures the suture cuff in a groove, formed in the outside wall 26 of the prosthetic heart valve.

SUMMARY OF THE INVENTION

A prosthetic heart valve having an orifice is configured to allow blood flow through the orifice. A suture cuff extends around an outer circumference of an outer ring. The suture cuff is adapted for attachment to a native tissue annulus of a patient. A weld between the suture cuff and the ring is configured to attach the suture cuff to the ring.

DETAILED DESCRIPTION OF THE PREFERRED EMBODIMENTS

Figure 1:
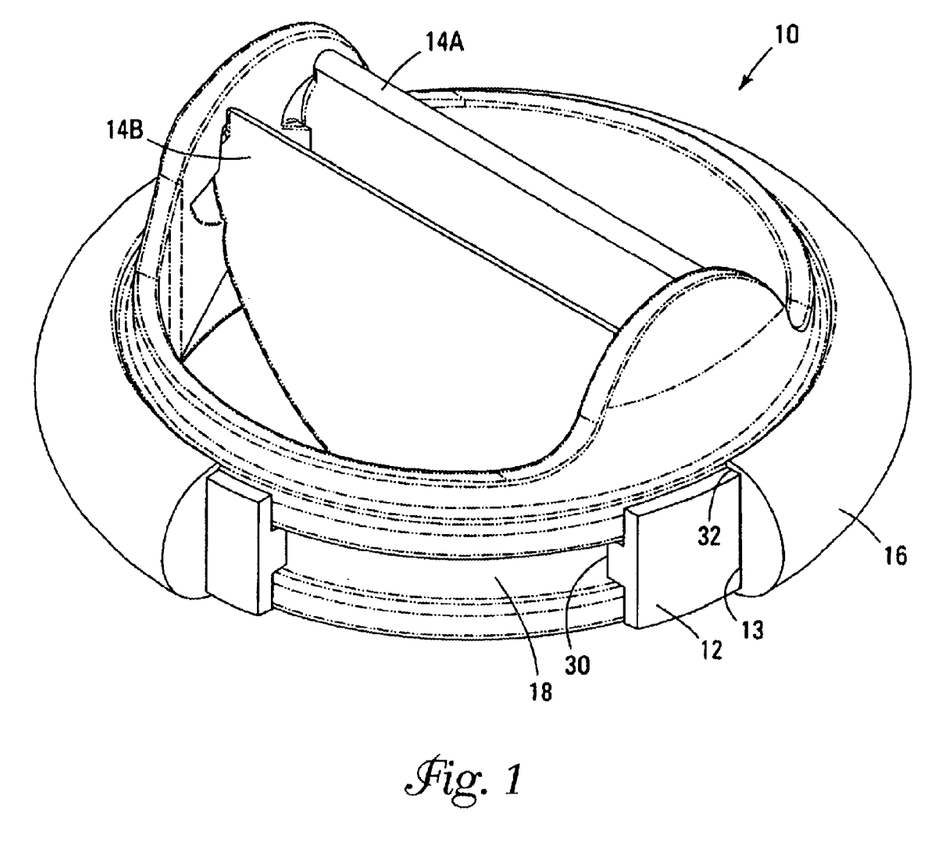
FIG. 1 is a perspective view of a prosthetic heart valve in accordance with the present invention.

FIG. 1 is a cut away perspective view of a prosthetic heart valve 10 in accordance with one embodiment of the present invention. Prosthetic heart valve 10 includes inner orifice 18 which carries occluders or leaflets 14A and 14B therein and outer ring 12. Occluders 14A and 14B pivot about a pivot axis and are configured to allow blood flow in a direction from the top of the page toward the bottom of the page and block blood flow in the opposite direction. A sewing or suture cuff 16 extends around an outer circumference of the valve and is attached to the valve is accordance with welding techniques of the present invention. In one aspect, the outer ring directly carries an occluding mechanism and does not require an inner orifice.

In one aspect of the present invention, the attachment of the suture cuff 16 to the ring 12 shown in FIG. 1 is preferably implemented in heart valve prostheses which have an outer ring 12 and an inner orifice 18. The inner orifice 18 can be attached to the outer ring 12 through any appropriate technique, such as a snap fit into rims. In one preferred embodiment, the outer ring 12 can be rotated relative to the inner orifice 18 through application of a controlled torque between the two pieces, allowing the surgeon to orient the occluders in the optimum position. The torque required to cause rotation can be selected by adjusting the tolerances between the ring 12 and the orifice 18.

Figure 2:
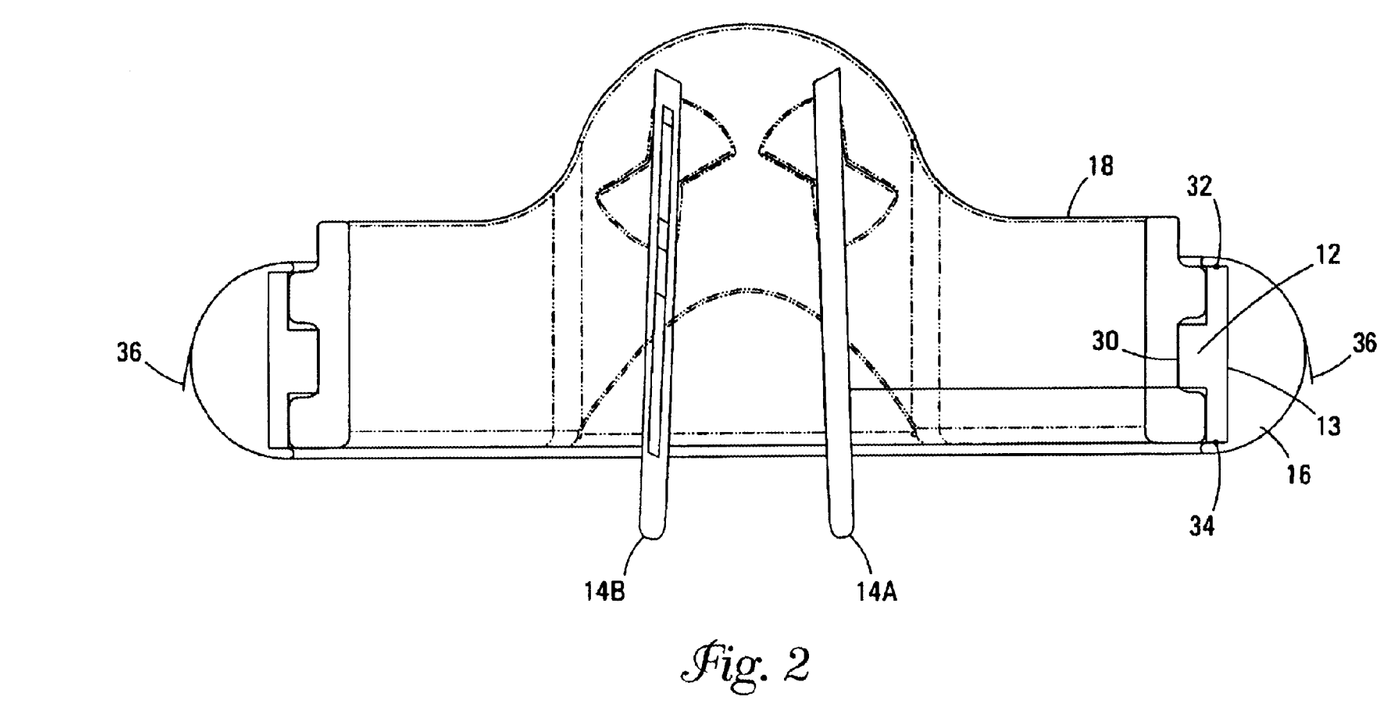
FIG. 2 is a cross-sectional view of the prosthetic heart valve of FIG. 1.

FIG. 2 is a side cross-sectional view of valve 10 showing attachment of cuff 16 in greater detail. Outer ring 12 includes an interior ridge or protrusion 30 adapted for coupling to inner orifice 18. In accordance with aspects of the present invention, cuff 16 is coupled to outer ring 12 through welding, such as ultrasonic welding. Cuff 16 is attached at weld surfaces 32 and 34, and/or to surface 13, such that the weld extends around the circumference of ring 12. The ends 36 of cuff 16 are attached to one another through suturing or welding.

In one preferred embodiment of the present invention, weld surfaces 32 and 34 are formed through an ultrasonic welding technique. Preferably, ring 12 has a melting point similar to the melting point of suture cuff 16. In such an embodiment, the cuff 16 can be directly bonded to the ring 12. In one preferred embodiment, a horn of the ultrasonic welder has a circular end configured to make welds 32 and 34 along the entire circumference of ring 12. This allows weld 32 or 34 to be formed in a single step. Alternatively, a series of spot welds can be employed. The horn of the ultrasonic welder is preferably beveled on the inside diameter such that the square edge of ring 12 can act as an energy concentrator to focus the ultrasonic energy to a small area. This technique works well for bonding to the fabric which is thin and fragile. In one embodiment, an ultrasonic signal of about 15 kHz to about 45 Hz is used having a signal strength output of about 150 watts to about 3300 watts for between about 1 second and about 30 seconds. One such ultrasonic welder is the 2000d Ultrasonic Welder available from Branson.

In ultrasonic welding, an ultrasonic signal is used to cause a material to vibrate. This transfers energy into the material and friction due to the resulting vibration causes the material to heat. Advantageously, the ultrasonic weld occurs at the interface between the suture cuff 16 and the ring 12. The ultrasonic signal vibrates the fabric causing friction between the cuff 16 and ring 12. This melts the fabric and ring concurrently, bonding them together. When they cool, the fabric material and ring 12 material have melted together, forming the weld. In one preferred embodiment, both the ring 12 and the cuff 16 are fabricated of a polyester, such as PET (polyethylene terephthlate). Inner orifice 18 can comprise pyrolytic carbon or a metal, such as titanium. Alternatively, if orifice 18 comprises a polymeric material, cuff 16 can be welded directly to orifice 18 without requiring use of ring 12.

Figure 3:
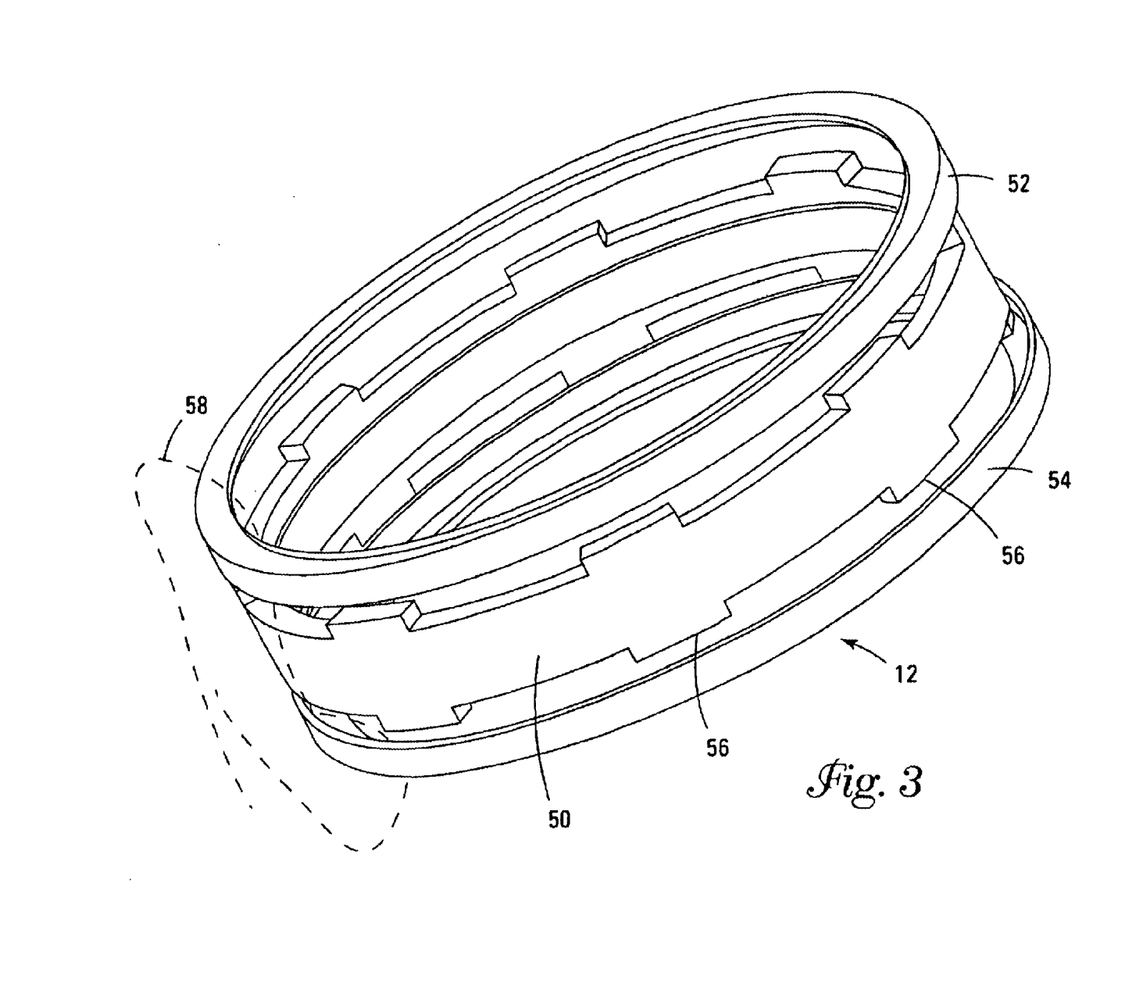
FIG. 3 is an exploded perspective view of another embodiment of the outer ring of the prosthetic heart valve of FIG. 1.
Figure 4:
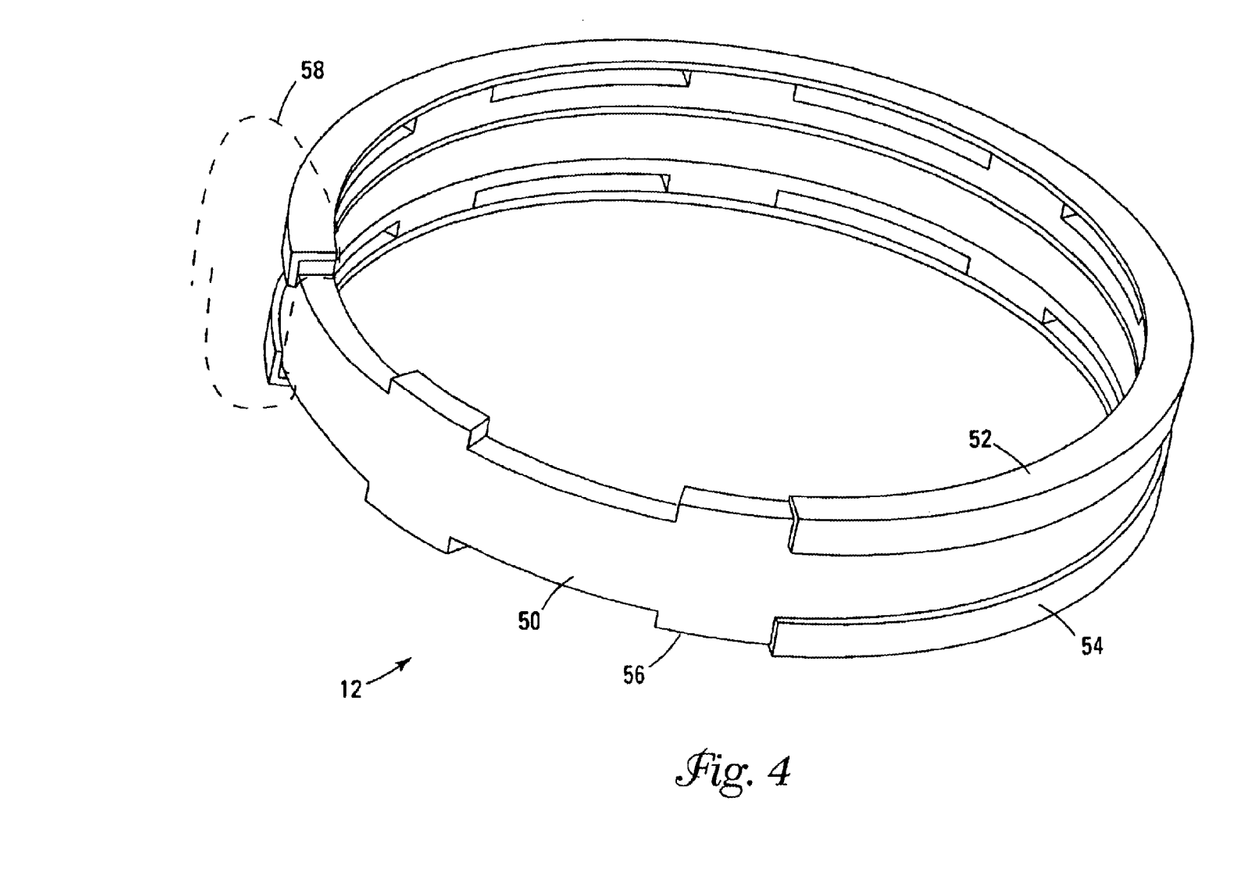
FIG. 4 is an assembled perspective view of the outer ring of FIG. 3.

In another aspect of the invention, a set of fabric capturing bands, such as bands 52 and 54, are used to attach the cuff 16 to the ring 12. Such an embodiment is particularly advantageous when the outer ring 12 is fabricated of a material, which has a higher melting point than that of cuff 16. FIG. 3 is an exploded perspective view and FIG. 4 is a cut away assembled perspective view of this second embodiment of outer ring 12. In the embodiments of FIGS. 3 and 4, ring 50 is sandwiched between fabric capturing bands 52 and 54. Bands can be joined as a single, integral unit 52, or can be separate bands 52, 54. In one preferred embodiment, bands 52, 54 are L-shaped. In another preferred embodiment, integral band 52 is C shaped. Ring 50 includes a number of spaced apart protrusions 56 distributed around the ring 50. The shape, height, width and number of protrusions 56 can vary as appropriate. The rings 50, 52 and 54 can be of the same material, but the cuff fabric 16 is different. As illustrated in FIGS. 3 and 4, the fabric of cuff 16 follows the path shown by dashed line 58 and is positioned along the inner radius of bands 52 and 54 and the outer radius of ring 50. Protrusions 56 can also be incorporated into the stent shown in FIG. 6A.

Figure 5:
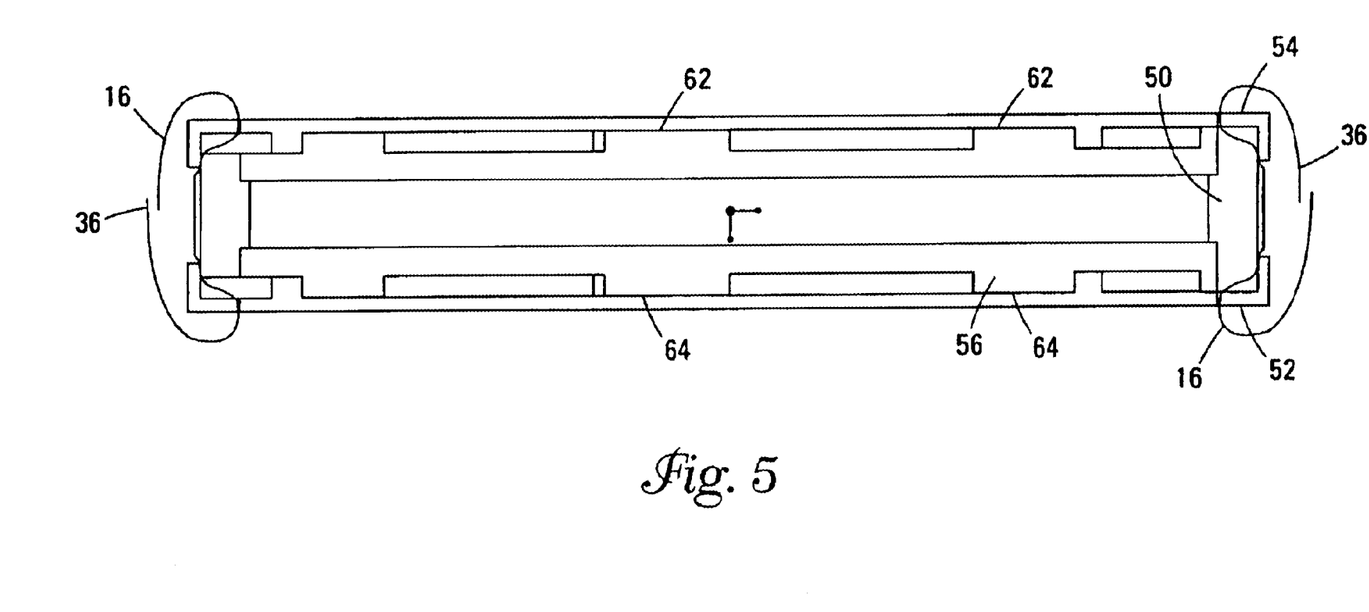
FIG. 5 is a side cross-sectional view of the outer ring of FIG. 3.

As illustrated in the cross-sectional view of FIG. 5, in the second embodiment of the invention, bands 52 and 54 are covered by suture cuff 16. Bands 52 and 54 are fabricated from the same material as ring 50. Ultrasonic welds 62 and 64 are used to attach bands 52 and 54 to ring 50. The bonding occurs at protrusions 56. The cuff melts at protrusion 56 while the cuff in the regions between protrusions 56 still has integrity and is not weakened. This allows the bonding points of the weld to be spaced apart around the circumference of the rings. For example, in such an embodiment, ring 50, 52 and 54 can be formed of any weldable polymer, such as PEEK (polyetheretherketone). Cuff 16 is formed of a polyester material, such as PET. Since the fabric of cuff 16 has a lower melting point than ring 50 or bands 52, 54, it is only selectively melted at protrusions 56. Ring 50 and bands 52, 54 melt together capturing the fabric of cuff 16 in the process.

Figure 6A:
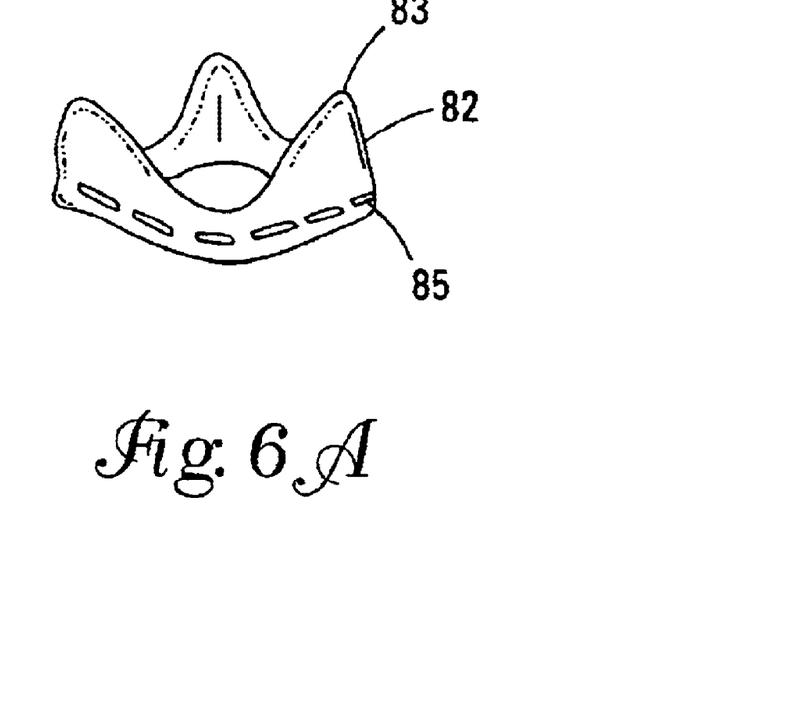
FIG. 6A is a side view of a polymer stent and FIG. 6B is a side view of a bioprosthetic heart valve in accordance with the present invention.
Figure 6B:
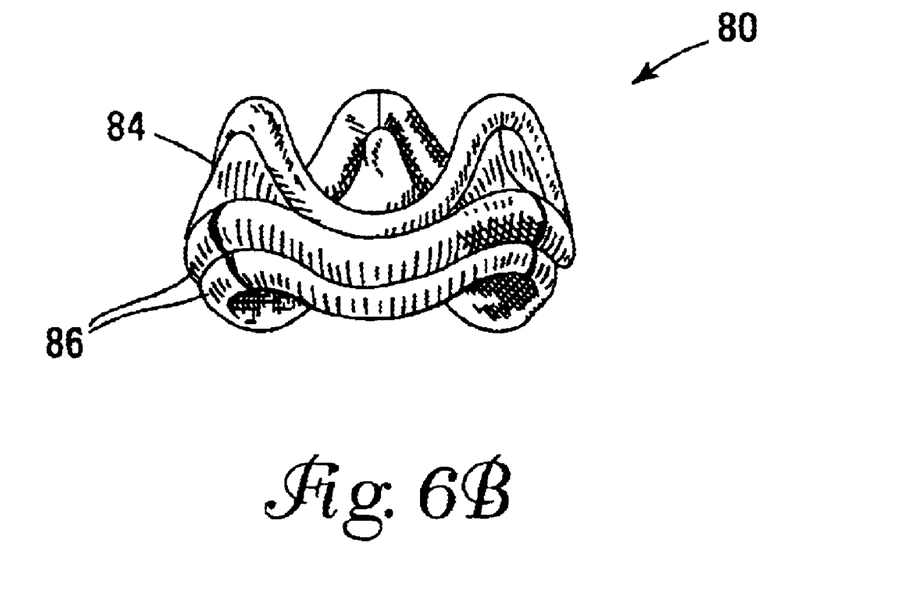

The present invention of both embodiments (ring 12 and ring 50 with bands 52, 54) is also applicable to bioprosthetic heart valves such as valve 80 shown in FIG. 6B. FIG. 6A is a side view of a polymer stent 82, which is welded to fabric 84 shown in the side view of bioprosthetic valve 80 of FIG. 6B. Further, suture cuff 86 can also be welded in accordance with the invention. The weld can be at commissures 83 or along the base 85 of stent 82. The valve 80 can be of tissue, an allograft, or a polymer, such as polyurethane. Polymer stent 82 can be made, for instance, from PET or PEEK.

Figure 7:
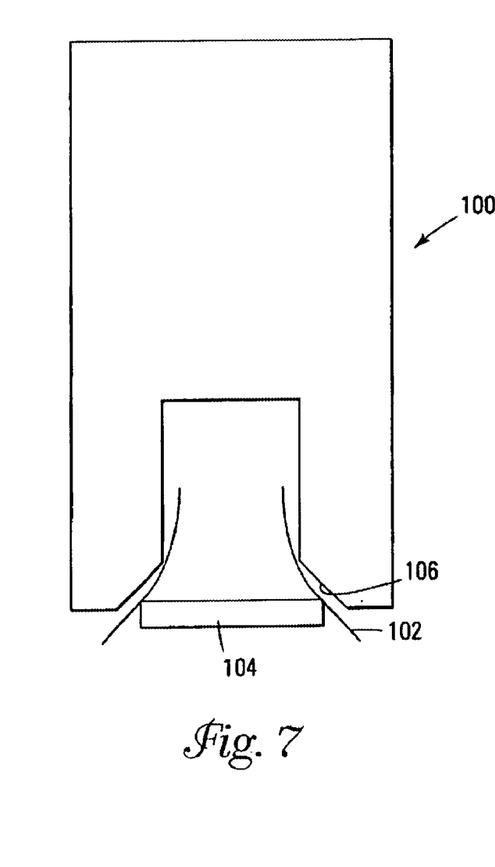
FIG. 7 is a side plan view showing a step of forming a weld using an ultrasonic welding horn in accordance with one embodiment of the present invention.

FIG. 7 is a side plan view, which illustrates a welding step in accordance with one embodiment of the present invention. In FIG. 7 an ultrasonic titanium horn 100 is pressed against fabric 102 and ring 104. Horn 100 is adapted to uniformly apply pressure against ring 104 using beveled surface 106. This allows a weld to be formed around the entire circumference of ring 104 in a single step.

Figure 8A:
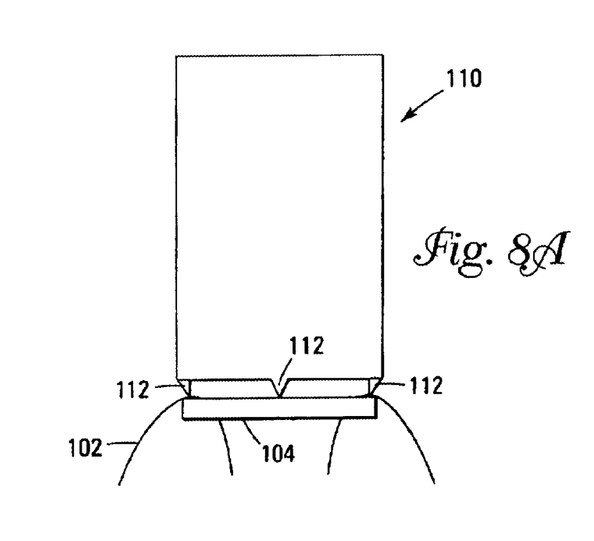
FIG. 8A is a side plan view showing another embodiment of an ultrasonic welding horn.
Figure 8B:
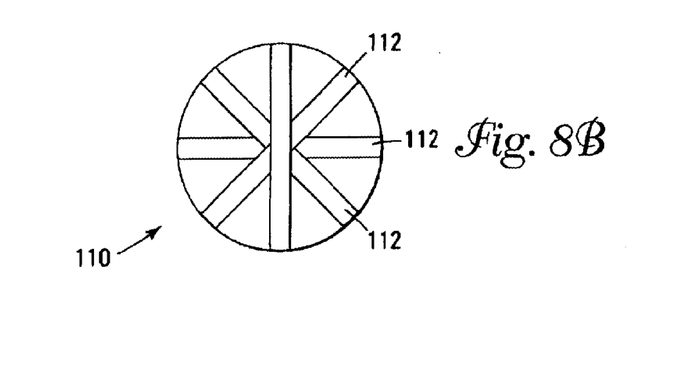
FIG. 8B is a bottom plan view of the ultrasonic welding horn of FIG. 8A.

FIG. 8A is a side plan view and FIG. 8B is a bottom plan view of an ultrasonic welding horn 110 in accordance with another embodiment. Horn 110 includes a plurality of protrusions 112 which form spot welds between fabric 102 and ring 104. This configuration allows a plurality of spot welds to be formed in a single welding step.

The use of ultrasonic welding eliminates the requirement for any additional clip mechanism or device to attach the cuff to the outer ring or orifice. This reduces the space required for the attachment of the cuff to the ring or any aspect of the valve, thereby allowing placement of a bigger valve in the patient's annulus. Further, the welding requires less valve assembly time than prior art designs, uses less radial space and provides an improved bond between the ring and the cuff. The weld effectively provides a unitary or integral piece without any secondary material used for adhesion. This method of assembly is less intensive since suture winds and secondary material, such as adhesives or springs, are not necessary.

Although the present invention has been described with reference to preferred embodiments, workers skilled in the art will recognize that changes may be made in form and detail without departing from the spirit and scope of the invention.

What is claimed is:

1. A prosthetic heart valve, comprising,
    an outer orifice ring configured to allow blood flow therethrough;
    a first outer band adjacent a periphery of the outer orifice ring;
    a suture cuff including a fabric which extends around an outer circumference of the ring, the fabric being between the outer orifice ring and the first outer band, the suture cuff adapted for attachment to a native tissue annulus of a patient; and
    a weld which bonds the outer orifice ring to the first outer band to thereby attach the suture cuff to the outer orifice ring, the weld extending through the fabric.

2. The prosthetic heart valve of claim 1 further comprising a second outer band opposing the first outer band, the outer orifice ring positioned between the first and second outer bands and wherein the weld is between the two outer bands and the ring.

3. The prosthetic heart valve of claim 1 wherein a cross-section of the first outer band has a substantial L-shape.

4. The prosthetic heart valve of claim 1 wherein the outer orifice ring has a plurality of protrusions and the weld is positioned between the protrusions and the first outer band.

5. The prosthetic heart valve of claim 1, the first outer band having an inner surface corresponding to its inner circumference, the outer orifice ring having an outer surface corresponding to its outer circumference, wherein the fabric of the suture cuff extends between the inner surface of the outer band and an outer surface of the outer orifice ring.

6. The prosthetic heart valve of claim 1 wherein the outer orifice ring comprises a material, the outer orifice ring material and the fabric of the suture cuff having differing melting points.

7. The prosthetic heart valve of claim 1 wherein the first outer band comprises a material, the material of the first outer band and the material of the outer orifice ring comprising the same material.

8. The prosthetic heart valve of claim 1 wherein the weld comprises an ultrasonic weld.

9. The prosthetic heart valve of claim 1 wherein the outer ring and the suture cuff are formed from materials having substantially the same melting point.

10. The prosthetic heart valve of claim 1 further comprising an inner orifice configured to fit into the outer orifice ring, the inner orifice carrying an occluder mechanism.

11. The prosthetic heart valve of claim 10 wherein the outer orifice ring is configured to allow rotational movement relative to the inner orifice.

12. The prosthetic heart valve of claim 10 wherein the outer orifice ring comprises an occluding mechanism.

13. A method of making a prosthetic heart valve, comprising:

obtaining an outer orifice ring, the outer orifice ring configured to allow blood flow therethrough;

positioning a suture cuff having fabric around an outer circumference of the outer orifice ring, the suture cuff adapted for attachment to a native tissue annulus of a patient through suturing;

positioning a first, outer band along a periphery of the outer orifice ring adjacent the suture cuff such that the fabric of the suture cuff surrounds the first outer band and extends between the first outer band and the outer orifice ring; and welding the first outer band to the outer orifice ring through the fabric.

14. The method of claim 13 wherein welding the suture cuff comprises ultrasonic welding.

15. The method of claim 13 further comprising positioning a second outer band adjacent the suture cuff such that the fabric of the suture cuff surrounds the second outer band and extends between the second outer band and the outer orifice ring.

16. The method of claim 13 wherein the first outer band has a cross section with a substantial L-shape.

17. The method of claim 13 wherein the outer orifice ring includes a plurality of protrusions and the weld is between the protrusions and the first outer band.

18. The method of claim 13 wherein the suture cuff comprises fabric and the weld is between the fabric and the outer ring.

19. The method of claim 13 including providing an inner orifice configured to fit into the outer ring, the inner orifice carrying an occluder mechanism.

20. The method of claim 19 wherein the fit between the outer ring and the inner orifice allows relative rotation therebetween.

21. The method of claim 19 wherein the fit between the outer ring and the inner orifice allows relative rotation therebetween.

22. The method of claim 13 wherein the outer ring is configured to directly carry an occluder.

23. The method of claim 13 wherein the outer ring is configured to directly carry an occluder.

24. A prosthetic heart valve, comprising:

an outer orifice ring configured to allow blood flow therethrough;

a suture cuff comprising a fabric extending around an outer circumference of the ring, the fabric being positioned between the outer orifice ring and the suture cuff, the suture cuff adapted for attachment to a native tissue annulus of a patient; and a weld of the fabric of the suture cuff to the outer ring which bonds the fabric of the suture cuff directly to the outer ring to thereby attach the suture cuff to the outer ring.

25. The prosthetic heart valve of claim 24 wherein the fabric surrounds the outer orifice ring.

26. The prosthetic heart valve of claim 25 further including a first outer band, the outer ring positioned between the outer band.

27. The prosthetic heart valve of claim 26 wherein a cross-section of the outer band has a substantial L-shape.

28. The prosthetic heart valve of claim 26 wherein the band has a plurality of protrusions.

29. The prosthetic heart valve of claim 26 wherein the suture cuff extends through an inner circumference of the outer band and an outer circumference of the outer ring.

30. The prosthetic heart valve of claim 26 wherein the outer orifice ring and the fabric of the suture cuff have differing melting points.

31. The prosthetic heart valve of claim 25 wherein the fabric of the suture cuff and the outer orifice ring comprise the same material.

32. The prosthetic heart valve of claim 24 wherein the weld comprises an ultrasonic weld.

33. The prosthetic heart valve of claim 24 wherein the outer ring and the fabric of the suture cuff are formed from materials having substantially the same melting point.

34. The prosthetic heart valve of claim 24 further including an inner orifice configured to fit into the outer ring, the inner orifice carrying an occluder mechanism.

35. The prosthetic heart valve of claim 34 wherein the outer ring is configured to allow rotational movement relative to the inner orifice.

36. The prosthetic heart valve of claim 24 including an occluding mechanism directly carried by the outer ring.

37. A method of making a prosthetic heart valve, comprising:

obtaining an outer orifice ring, the outer orifice ring configured to allow blood flow therethrough;

positioning fabric of a suture cuff around an outer circumference of the outer orifice ring, the fabric being positioned between the outer orifice ring and the suture cuff, the suture cuff adapted for attachment to a native tissue annulus of a patient; and welding fabric of the suture cuff directly to the outer orifice ring to thereby attach the fabric of the suture cuff and to the outer orifice ring.

38. The method of claim 37 wherein welding the fabric comprises ultrasonic welding.

39. The method of claim 37 including placing a band in the suture cuff.

40. The method of claim 39 wherein there are two outer bands.

41. The method of claim 39 wherein the outer band has a cross section with a substantial L-shape.

42. The method of claim 37 wherein the outer ring includes a plurality of protrusions.

43. The method of claim 37 including providing an inner orifice configured to fit into the outer ring, the inner orifice carrying an occluder mechanism.

* * * * *